United States Patent
Lindgren et al.

(10) Patent No.: US 7,130,040 B2
(45) Date of Patent: Oct. 31, 2006

(54) METHOD FOR CONTINUOUS DETERMINATION OF THE PROPERTIES OF A FLOW OF WOOD FIBRES FOR FABRICATION OF FIBREBOARD

(75) Inventors: Thore Lindgren, Örnsköldsvik (SE); Johan Carlsson, Sundsvall (SE); Ulrika Backlund, Sundsvall (SE)

(73) Assignee: Valmet Fibertech AB (SE)

( * ) Notice: Subject to any disclaimer, the term of this patent is extended or adjusted under 35 U.S.C. 154(b) by 89 days.

(21) Appl. No.: 10/220,073

(22) PCT Filed: Mar. 1, 2001

(86) PCT No.: PCT/SE01/00441

§ 371 (c)(1),
(2), (4) Date: Aug. 27, 2002

(87) PCT Pub. No.: WO01/65237

PCT Pub. Date: Sep. 7, 2001

(65) Prior Publication Data

US 2003/0048440 A1    Mar. 13, 2003

(30) Foreign Application Priority Data

Mar. 2, 2000    (SE)    .................................... 0000694

(51) Int. Cl.
*G01J 3/00*    (2006.01)
(52) U.S. Cl. ...................................... 356/300; 162/198
(58) Field of Classification Search ................. 356/300; 162/198
See application file for complete search history.

(56) References Cited

U.S. PATENT DOCUMENTS 3,668,286 A * 6/1972 Brooks et al. .............. 264/451
5,397,406 A * 3/1995 Vaders et al. ............... 264/293
5,680,321 A * 10/1997 Helmer et al. ................ 702/30
6,187,145 B1 * 2/2001 Furumoto et al. .......... 162/198
6,398,914 B1 * 6/2002 Furumoto .................... 162/198

FOREIGN PATENT DOCUMENTS

| EP | 0 344 697 A2 | 12/1989 |
| EP | 0 967 326 A2 | 12/1999 |
| SE | 405 172 A1 | 11/1978 |
| WO | WO 84/01325 * | 4/1984 |
| WO | WO-95/31710 A1 | 11/1995 |
| WO | WO-97/04299 A1 | 2/1997 |
| WO | WO-98/28486 A1 | 7/1998 |
| WO | WO-99/45367 A1 | 9/1999 |

OTHER PUBLICATIONS

Hoskuldsson, Agnar, "PLS Regression Methods", Journal of Chemomentrics, vol. 2, pp. 211-228, 1988.

(Continued)

*Primary Examiner*—Hwa (Andrew) Lee
*Assistant Examiner*—Kara Geisel
(74) *Attorney, Agent, or Firm*—Lerner, David, Littenberg, Krumholz & Mentlik, LLP

(57) ABSTRACT

Methods for the continuous determination of the properties of a flow of wood fibers for use in the production of fiberboard are disclosed including determining reference value characteristics for calibration samples of the fibers, determining predetermined relationships between those reference value characteristics and measured spectral values for the fibers utilizing multivariant statistical regression methods, measuring reflectance spectral values for the fibers illuminated by light, and determining the fiber characteristics relating to the properties from the measured spectral values utilizing the predetermined relationship.

5 Claims, 1 Drawing Sheet

OTHER PUBLICATIONS

Wold, S., et al. "Principal Component Analysis", Chemometrics and Intelligent Laboratory Systems, vol. 2, pp. 37-52, 1987.

Geladi, Paul, et al. "Partial Least-Squares Regression: A Tutorial", Analytica Chimica Acta, vol. 185, pp. 1-17, 1986.

Meder, R., et al. "Prediction of wood chip and pulp and paper properties via multivariate analysis of spectral data", Appita Conference, May 2-6, 1994, pp. 479-484.

Wold, S., et al. "PLS—Partial Least-Squares Projections to Latent Structures", Institute of Chemistry, Umea University, S-90187 Umea, Sweden, pp. 523-550.

* cited by examiner

METHOD FOR CONTINUOUS DETERMINATION OF THE PROPERTIES OF A FLOW OF WOOD FIBRES FOR FABRICATION OF FIBREBOARD

FIELD OF THE INVENTION

The present invention relates to a method for the continuous determination of the properties of a flow of wood fibers for fabrication of fiberboard.

BACKGROUND OF THE INVENTION

Properties such as fiber moisture content, resin content, optical characteristics and fiber characteristics, such as shives and fiber length distribution, are generally known to affect the quality and properties of the finished fiberboard. Appropriate and, in particular, a stable fiber moisture content facilitates, e.g. checks on the pressing phase of panel fabrication and creates conditions for good control of the density profile of these panels.

After the panel is pressed, the resin added during panel fabrication hardens and creates, with the fiber network, a strong fiber composite structure. The resin is added either by injection into the blower line after the defibering process or into a mechanical resin mixer after the drying phase. The resin content has a major impact on the finished panel's strength properties, such as bending strength and tensile strength. The resin content is often governed by the specific properties the finished panel is to have. However, an excessive amount of resin is often dispensed in order to ensure the desired level of quality, as there is no way to accurately control other factors, such as fiber moisture, fiber length distribution and density, factors which also affect the properties of the finished fiberboard.

To date, the way in which fiber properties (such as the fiber length distribution and shives content) should be specified in order for the fiber network to optimally achieve the desired properties for the finished fiberboard has been unclear. One reason for this is because of the previous unavailability of any simple and rapid measurement method for determining and characterising fiber length distribution for MDF (medium density fiberboard) fibers. However, equipment is now available for determining and characterising fiber properties with the aid of image analysis. This is a complex technique, however, which is only practical in a laboratory environment, and which is definitely unsuitable for on-line measurement in the fabrication of MDF.

Since no facilities have hitherto been available for continuous on-line measurement of parameters for fiber characterisation during fiberboard fabrication, studying the way in which fiber properties should be devised in order to manufacture finished panels with the desired properties in an optimal fashion has been very difficult. This also applies to efforts to achieve optimal control of the defibering process so that the desired fiber properties are attained.

The need for resin can be minimized, and the production costs reduced, when fiber properties are controlled. Resin accounts for about one-third of the direct cost of fiberboard fabrication. Resin coating, i.e. the distribution of resin on the wood fibers, is also affected by the distribution of fiber lengths. Fine fiber fractions require more resin than the thicker fibers. As a result, increasing the resin content does not produce the anticipated increase in the strength of the finished panel when the fiber length distribution of the fibers used is inappropriate.

Multivariate analysis of spectral data for determining wood chip components, such as Klason lignin, extract and the total amount of carbohydrates, is described in "Dialog Information Services," File 248, PIRA, Dialog accession No. 00393878/5, PIRA accession No. 20017450, Meder R. et al.: "Prediction of wood chip and pulp and paper properties via multivariate analysis of spectral data," Melbourne, Australia, 2–6 May 1994, pp. 479–484, which is incorporated herein by reference thereto. In this article, Principal Component Analysis (PCA) and Principal Component Regression (PCR) were used for analysing near-infrared (NIR) spectra, Fourier-transformed infrared (FTIR) spectra and nuclear magnetic resonance (NMR) spectra taken from examined wood chips.

International Patent Application No. WO 97/04299 describes multivariate data analysis of near-infrared (NIR) spectra taken from raw materials, such as sawdust, shavings and wood chips, used for manufacturing chip board. Use of the measured values for controlling panel fabrication is also described. One of the objectives of the present invention is to refine this technique, based on multivariate analysis of spectral data, so it can also be used for continuous determination of the properties of wood fibers for fiberboard fabrication, these properties being of decisive importance to the properties of the finished panel.

SUMMARY OF THE INVENTION

This and other objects of the present invention have now been achieved by the discovery of a method for the continuous determination of the properties of a flow of wood fibers for use in the production of fiberboard comprising determining reference value characteristics for calibration samples of the fibers, determining predetermined relationships between the reference value characteristics relating to the properties and measured spectral values for the fibers utilizing multivariate statistical regression methods, measuring reflectance spectral values for the fibers illuminated by light, and determining the fiber characteristics relating to the properties from the measured spectral values utilizing the predetermined relationships. In a preferred embodiment, the light comprises a light spectra in the wave length range of from 400 to 2,500 nm.

In accordance with one embodiment of the method of the present invention, the calibration samples of the fibers are prepared utilizing a set of test variables selected to obtain a predetermined range of the fiber characteristics. In accordance with another embodiment of the method of the present invention, a plurality of the fiber characteristics are determined from one of the measured reflectance spectral values. Preferably, the plurality of the fiber characteristics includes the resin content, the fiber moisture content, and the optical properties of the flow of wood fibers.

In accordance with another embodiment of the method of the present invention, the method includes producing the flow of wood fibers in a fiber preparation process, and controlling the fiber preparation process by means of the determined fiber characteristics in order to control the desired characteristics of the wood fibers. In a preferred embodiment, the fiber preparation process comprises a refining process including a defibering step, and the determined fiber characteristics are used to control the defibering step.

In accordance with the method of the present invention, continuous determination of fiber length distribution greatly enhances the ability to control the fabrication process and optimize the cost of that process, primarily by always dispensing the precise amount of resin which is required. In addition, continuous feedback from the measured fiber length distribution to the defibering process also becomes possible for controlling this process. On-line quality control of fiber properties, something which has hitherto been impossible in the fabrication of fibers for fiberboard, is achieved in this way. In addition, determination of the quantity of resin, in the flow of resin-coated fibers, from the reflectance spectrum supplies continuous information on both the total amount of resin dispensed, a previously per se possible determination, and on the distribution of the resin on the fibers. The moisture content of fibers in the fiber flow, which can be obtained from the reflectance spectrum with the method according to the present invention, is an important parameter in the fabrication of fiberboard. In addition, the brightness/color of the fiber flow can be continuously determined. The brightness/color of the fiber flow is also a measure of the effect of thermal pre-treatment on the chips or fibers, and additionally supplies information on the brightness/color of the finished product.

According to one advantageous embodiment of the method according to the present invention, light spectra in the 400 to 2500 nm wavelength range are used. Primarily, two physical processes make the study of this wavelength range especially suitable for determining the quality properties of the fiber flow, namely, energy absorption and light scattering. Near-infrared (NIR) spectroscopy is based on electromagnetic radiation in the 700 to 2500 nm wavelength range. Mainly organic substances containing C—H, O—H and N—H bonds, which absorb the radiation, lie within this range. The energy mainly excites harmonics and combinations of rotating and vibrating states. Organic material absorbs less energy in the NIR range than in the UV and IR range. As a result, near-infrared light penetrates more deeply into the sample. A non-homogenous material, such as wood fibers, induces a scattering of light related to the size of the particles. This property, plus molecular vibrations and rotations, make it possible to characterise the size distribution of the fibers in the fiber flow, i.e. to determine the fiber length distribution.

According to additional advantageous embodiments of the method according to the present invention, a reference distribution of fiber length is established for calibration samples of the fiber flow. The same calibration samples are also used for determining fiber length distribution from the measured reflectance spectrum, and these lengths are modelled in a calibration procedure against the reference fiber length distribution with the aid of multivariate statistical regression methods for determining the predetermined relations between measured spectral values and fiber length distribution. The reference fiber length distribution is suitably determined by means of a standardised method. In an analogous way, the predetermined relations between measured spectral values and reference values for resin content, fiber moisture and optical properties are determined, the reference value for resin content then being appropriately established by determination of the nitrogen content of nitrogenous resin by means of the Kjeldahl method, the reference value for fiber moisture being determined by drying and weighing the calibration samples, and the reference value for optical properties being determined according to the ISO Brightness norm.

According to another advantageous embodiment of the method according to the present invention, one or more of the parameters derived from the reflectance spectrum, i.e. fiber length distribution, resin content, fiber moisture and optical properties, is/are used in a feedback procedure for on-line control of the fiber preparation process in order to impart the desired properties to the wood fibers used. This makes possible continuous, overriding quality control of these parameters.

BRIEF DESCRIPTION OF THE DRAWING

The present invention will be more fully appreciated with reference to the following detailed description which, in turn, refers to the FIGURE which is a schematic representation of a method according to the present invention.

DESTAILED DESCRIPTION

Figure 1:
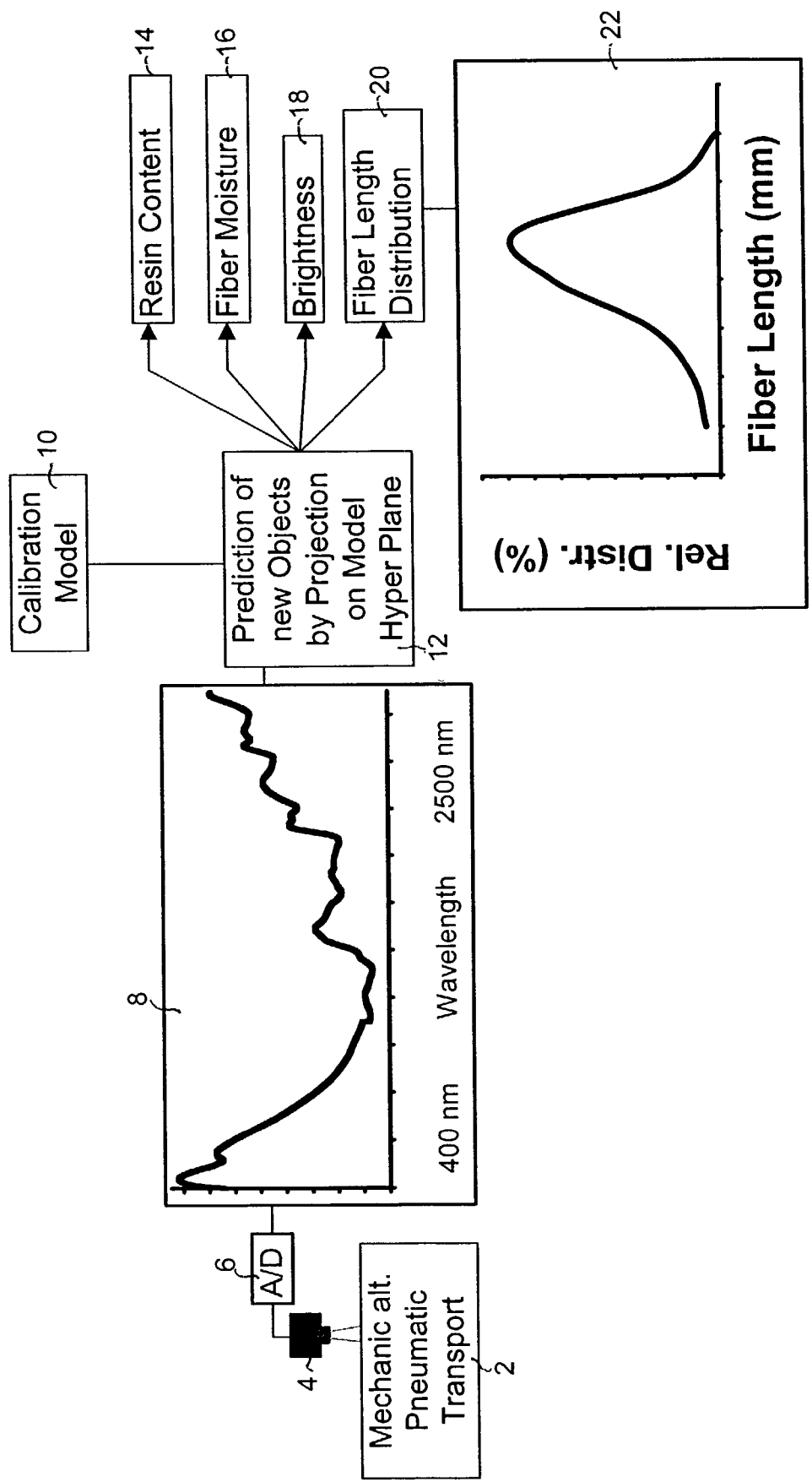

The FIGURE depicts mechanical or pneumatic transport 2 of a flow of wood fibers intended for use in fiberboard fabrication. The wood fiber is suitably prepared in a refiner process with a specific beating energy less than 500 kWh/h. At a measuring point, situated downstream of the defibering and drying process, the flow of fibers is illuminated with light of an appropriate wavelength, and the ensuing reflectance spectrum is picked up by a detector 4 in the 400–2500 nm wavelength range, i.e. in the visible (VIS) and near-infrared (NIR) range. The detected spectrum is A/D converted at 6. A typical conformation for the resulting spectrum is shown at 8 in the FIGURE The calibration required in the method according to the present invention is performed at 10 in the FIGURE in the following manner.

A number of calibration samples of fiber flow are prepared according to a test plan in which the level of the test variables is selected to produce a good spread in the values for properties of interest, namely, fiber length distribution, resin content, fiber moisture and optical properties. A calibration sample can encompass an operating period during full-scale production.

Reflectance spectra of the aforementioned kind are recorded for the calibration samples, and reference values are determined, using an appropriate laboratory method, for each of the aforesaid properties. Thus, fiber length distribution (and shives) can be determined with e.g. image analysis. Resin content can advantageously be determined with the Kjeldahl method in instances in which a nitrogenous resin is used. If e.g. phenol resin, which does not contain nitrogen, is used, some other appropriate method must be employed for determining reference values for the resin. Reference values for fiber moisture can be established using a drying and weighing procedure, and optical properties can be determined according to the ISO Brightness norm for determining light reflection. In the calculation unit 12 in the FIGURE, mathematical correlations can be established between spectra recorded for calibration samples of fiber flow and the corresponding reference values with the aid of multivariate statistical regression methods, preferably Principal Component Analysis (PCA) and Projection to Latent Structures (PLS) regression. This type of calculation is well-known, cf. e.g. Martens H. and Naes T., "Multivariate Calibration," Wiley & Sons, New York (1989); Wold S., Johansson E. and Cocchi M., "Partial Least Squares Projections to Latent Structures, in QSAR in drug design, "Theory, Methods and Application," Kubini H., Ed., (1993); Hoskuldsson A., "PLS Regression Methods," Journal of Chemometrics, vol. 2 (1988); Geladi P. and Kowalski B. R., Analytica Chimica Acta, 185 (1986) and Wold S., Esbensen K., and Geladi P., Principal Component Analysis, Chemometrics and Intelligent Laboratory Systems, 2 (1987), each of which are incorporated herein by reference thereto.

This creates a calibration model or a relation between the reference values and associated spectra, determined with appropriate laboratory methods, (quality variables (y) as a function of the spectrum (x) y=f(x)), the calibration procedure being carried out on a number of fiber flow samples with relatively good variation in the properties or parameter values, as noted above.

With the aid of relations established in this way, these parameters can be obtained from subsequently recorded reflectance spectra for the fiber flow. This achieves contactless, on-line measurement of fiber length distribution at 20 and 22, resin content at 14, fiber moisture at 16 and optical properties at 18 in the FIGURE. Thus, the four cited properties are determined in the same measurement procedure from a spectrum's information content.

The moisture content of wood fiber is normally from 5 to 20%, often from 10 to 20%.

The length of the fibers used in fabricating fiberboard is typically from 0.15 to 4 mm for spruce fibers, and the upper fiber length limit for wood with shorter fibers, such as beech, is about 3 mm.

In the method according to the present invention, fiber length distribution can be determined at a relatively large number of intervals for the lengths range in question. In the 0 to 7 mm length range, the method according to the present invention can determine fiber length distribution in intervals as small as 0.1 mm, i.e. the length range is subdivided into 70 intervals or fractions, cf. the distribution at 22 in the FIGURE.

The three parameters fiber length distribution, resin content and fiber moisture are of major importance for controlling quality and optimising the cost of fiberboard fabrication, as discussed above. Optical properties are also of interest, as the lightest possible board is normally desirable. Thus, this continuous, on-line measurement according to the method according to the present invention makes possible feedback and on-line quality control of fiber properties, something hitherto impossible in the fabrication of fiberboard. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for the continuous determination of the properties of a flow of wood fibers for use in the production of fiberboard comprising determining reference value characteristics for calibration samples of said fibers, determining predetermined relationships between said reference value characteristics relating to said properties and measured spectral values for said fibers utilizing multivariate statistical regression methods, measuring reflectance spectral values for said fibers illuminated by light, and determining said fiber characteristics relating to said properties from said measured spectral values utilizing said predetermined relationships, wherein said plurality of said fiber characteristics includes the resin content, the fiber moisture content, and the optical properties of said flow of wood fibers, said flow of wood fibers being in a fiber preparation process which is controlled based on said fiber characteristics, wherein the wood fibers include a moisture content of approximately from between 10% to 20%.

2. The method of claim 1 wherein said light comprises a light spectra in the wave length range of from 400 to 2,500 nm.

3. The method of claim 1 wherein said calibration samples of said fibers are prepared utilizing a set of test variables selected to obtain a predetermined range of said fiber characteristics.

4. The method of claim 1 wherein a plurality of said fiber characteristics are determined from one of said measured reflectance spectral values.

5. The method of claim 1 wherein said fiber preparation process includes a refining process including a defibering step, and wherein said determined fiber characteristics are used to control said defibering step.

* * * * *

UNITED STATES PATENT AND TRADEMARK OFFICE
CERTIFICATE OF CORRECTION

PATENT NO. : 7,130,040 B2  Page 1 of 1
APPLICATION NO. : 10/220073
DATED : October 31, 2006
INVENTOR(S) : Thore Lindgren, Johan Carlsson and Ulrika Backlund It is certified that error appears in the above-identified patent and that said Letters Patent is hereby corrected as shown below:

On the face of the patent, (54), "FIBRES" should read --FIBERS--.
On the face of the patent, (54), "FIBREBOARD" should read --FIBERBOARD--.
Column 1, line 3, "FIBRES" should read --FIBERS--.
Column 1, line 4, "FIBREBOARD" should read --FIBERBOARD--.
Column 2, line 47, after "characteristics." begin a new paragraph.
Column 4, line 50, after "reflection." begin a new paragraph.
Column 5, line 39, after "board." begin a new paragraph.

Signed and Sealed this

Sixth Day of March, 2007

JON W. DUDAS
*Director of the United States Patent and Trademark Office*